(12) United States Patent
Roberts et al.

(10) Patent No.: US 9,937,160 B2
(45) Date of Patent: Apr. 10, 2018

(54) THIENOPYRIDINE DERIVATIVE FOR THE TREATMENT OF HEPATITIS C INFECTIONS

(71) Applicant: Cipla (UK) Limited, Weybridge, Surrey (GB)

(72) Inventors: Karl Roberts, Llanelli (GB); Geena Malhotra, Mumbai (IN); Dhiraj Abhyankar, Mumbai (IN); Kalpana Joshi, Thane (IN); Jeevan Ghosalkar, Dombivali (East) (IN)

(73) Assignee: Cipla (UK) Limited, Mumbai (IN)

( * ) Notice: Subject to any disclaimer, the term of this patent is extended or adjusted under 35 U.S.C. 154(b) by 0 days.

(21) Appl. No.: 15/212,703

(22) Filed: Jul. 18, 2016

(65) Prior Publication Data

US 2017/0014394 A1    Jan. 19, 2017

(30) Foreign Application Priority Data

Jul. 16, 2015    (IN) .......................... 2691/MUM/2015

(51) Int. Cl.
  *A61K 31/44*     (2006.01)
  *A61K 31/4365*   (2006.01)
  *A61K 45/06*     (2006.01)

(52) U.S. Cl.
  CPC .......... *A61K 31/4365* (2013.01); *A61K 45/06* (2013.01)

(58) Field of Classification Search
  USPC ....................................................... 514/301
  See application file for complete search history.

(56) References Cited

U.S. PATENT DOCUMENTS

2009/0281136 A1* 11/2009 Mhetre ............... A61K 9/2009
                                                           514/301

OTHER PUBLICATIONS

Gonzalez-Reimers et al., Thrombin activation and liver inflammation in advanced hepatitis C virus infection, World J Gastroenterol (2016) 22(18) 4427-4437; May 14, 2016.
Assigner, Platelets and infection—an emerging role of platelets in viral infection, Frontiers in Immunology, vol. 5, Article 649; Dec. 18, 2014.

* cited by examiner

Primary Examiner — Shengjun Wang
(74) Attorney, Agent, or Firm — Meunier Carlin & Curfman LLC

(57) ABSTRACT

The present invention relates to methods of treatment of hepatitis C using prasugrel. The methods of the present invention can be used in patients with hepatitis C administering prasugrel in combination with one or more anti-hepatitis C drugs.

7 Claims, 2 Drawing Sheets

THIENOPYRIDINE DERIVATIVE FOR THE TREATMENT OF HEPATITIS C INFECTIONS

FIELD OF THE INVENTION

The present invention relates to method of treating Hepatitis C by administering a thienopyridine derivative alone or optionally in combination with one or more anti-hepatitis C drugs to a subject in need thereof. In particular, the present invention pertains to methods for the treatment of Hepatitis C viral infection in humans by administering Prasugrel alone or in combination with one or more anti-Hepatitis C drugs.

BACKGROUND

HCV (Hepatitis C virus) is a major cause of chronic liver disease. Hepatitis C virus is most commonly transmitted through exposure to contaminated blood. Due its widespread nature and global burden, this disease has always attracted attention for insight into its causative agent hepatitis C virus (HCV) and for the development of new therapeutic approaches. Even after twenty-four years from its discovery, HCV continues to be a major cause of concern and a huge burden on public health systems worldwide. WHO estimates that a minimum of 3% of the world's population is chronically infected with HCV. As cited in various research articles, HCV has caused massive impact on public health, and around 180 million people in the world are infected with HCV, with an estimated 3 to 4 million new infections global per year. It causes infection in two phases, first involves acute attack that last for few weeks; if untreated HCV may persist for long time which is termed as chronic hepatitis C. This chronic infection may often lead to chronic liver disease (CLD) that may ultimately lead to hepatic failure and hepato-cellular carcinoma.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B.

The main targets of the direct-acting antiviral agents are the HCV-encoded proteins that are vital to the replication of the virus. The infectious viral structure is comprised of envelope glycoproteins in a lipid bilayer that contain the viral core protein and RNA. After cell entry, the viral RNA is translated through host machinery into a polyprotein, which is cleaved during and after translation by both host and viral-encoded proteases into 10 mature viral proteins, including a number of nonstructural (NS) proteins. One of the viral proteases involved in this post-translational processing is a heterodimeric complex of the NS3 and NS4A proteins (NS3/NS4A). NS3 possesses the proteolytic activity and NS4 is a membrane protein that acts as a cofactor. Synthesis of new viral RNA occurs in a highly structured replication complex that consists of NS3, NS4A, NS4B, NS5A, and NS5B. NS5B is an RNA-dependent RNA polymerase that is essential for viral replication. NS5A has a presumptive role in the organization of the replication complex and in regulating replication. It is also involved in assembly of the viral particle that is released from the host cell. Direct-acting antivirals are inhibitors of the NS3/4A protease, the NS5A protein, and the NS5B polymerase.

HCV is characterized by an extremely high degree of variability. The genetic heterogeneity of HCV leads to multiple genomic variants allowing rapid selection of mutants that better adapts to environmental changes. This genetic heterogeneity is the basis of chronic infection which leads to limited treatment efficacy. The various available options for the treatment of hepatitis C are screening, surgery, liver transplant, radiation therapy, chemotherapy, virus therapy and targeted therapy. A number of potential molecular targets for drug development of direct-acting antivirals (DAAs) as anti-HCV therapeutics have now been identified including, but not limited to, the NS2-NS3 autoprotease, NS4A protease, the N3 protease, the N3 helicase, and the NS5B polymerase.

Currently approved standard of care ("SOC") for the treatment of chronic HCV infection is a combination therapy with pegylated interferon alfa-2a or pegylated interferon alfa-2b (collectively "peginterferon" or "PEG") used alone or in combination with ribavirin ("RBV"). Other FDA approved drugs for hepatitis C include Olysio® (simeprevir), Victrelis® (boceprevir), Sovaldi® (sofosbuvir), Epclusa (Sofosbuvir; Velpatasvir)®, Viekirax® (dasabuvir, ombitasvir, paritaprevir, ritonavir), Daklinza® (daclatasavir), Exviera® (dasabuvir), Harvoni®(Ledipasvir Sofosbuvir), Incivek® (telaprevir), Technivie® (ombitasvir; paritaprevir; ritonavir) Zepatier®(elbasvir; grazoprevir), Viekira Pak® (dasabuvir sodium; ombitasvir; paritaprevir; ritonavir) etc.

Challenges facing current treatment of HCV include lack of efficacy in patients with difficult—to-treat disease, such as patients with cirrhosis or infected with HCV genotype 1 (who represent a majority of US HCV infections), the toxicity of combination therapy, the difficulty of therapy, and the poor reception of these treatments by many patients. Moreover an attempt to invent new drugs for the treatment of HCV would be costly and time consuming. Thus, there is a need for new treatments and therapies for HCV infection to treat or ameliorate one or more symptoms of Hepatitis C. Accordingly, the current invention focuses on the existing pool of drugs which could be effective in the treatment of Hepatitis C with the ultimate goals of targeting the virus, viral resistance challenges, shortening the length of therapy, improving sustained virologic response rates, and minimizing side effects.

SUMMARY OF THE INVENTION

According to one aspect of the present invention, there is provided a method of treating Hepatitis C comprising administering a thienopyridine derivative wherein the thienopyridine derivative is prasugrel.

According to yet another aspect of the present invention, there is provided a method of alleviating or treating Hepatitis C by administration of prasugrel in combination with one or more anti-hepatitis C drugs.

According to yet another aspect of the invention, there is provided a pharmaceutical composition comprising prasugrel for the treatment of Hepatitis C.

According to another aspect of the present invention, there is provided a pharmaceutical composition comprising prasugrel in combination with one or more anti-hepatitis C drugs.

DETAILED DESCRIPTION OF THE INVENTION

Figure 1:
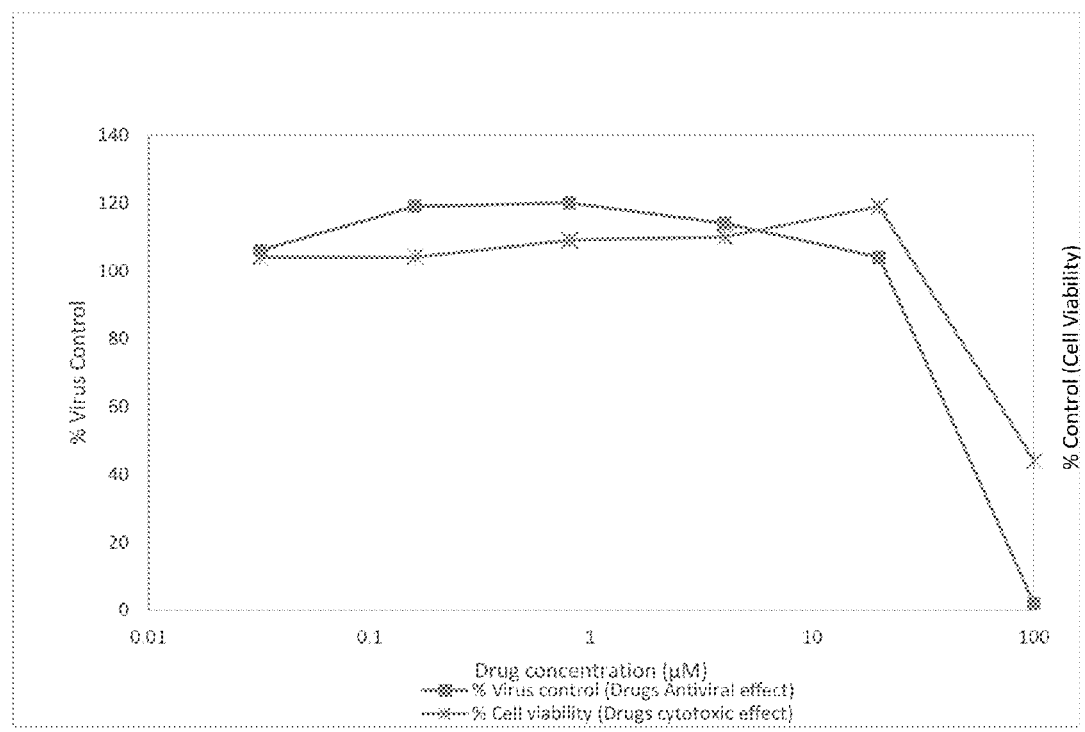
FIG. 1 includes a graph of Prasugrel in HCV GT1b CON-1 replicon assay.
Figure 2:
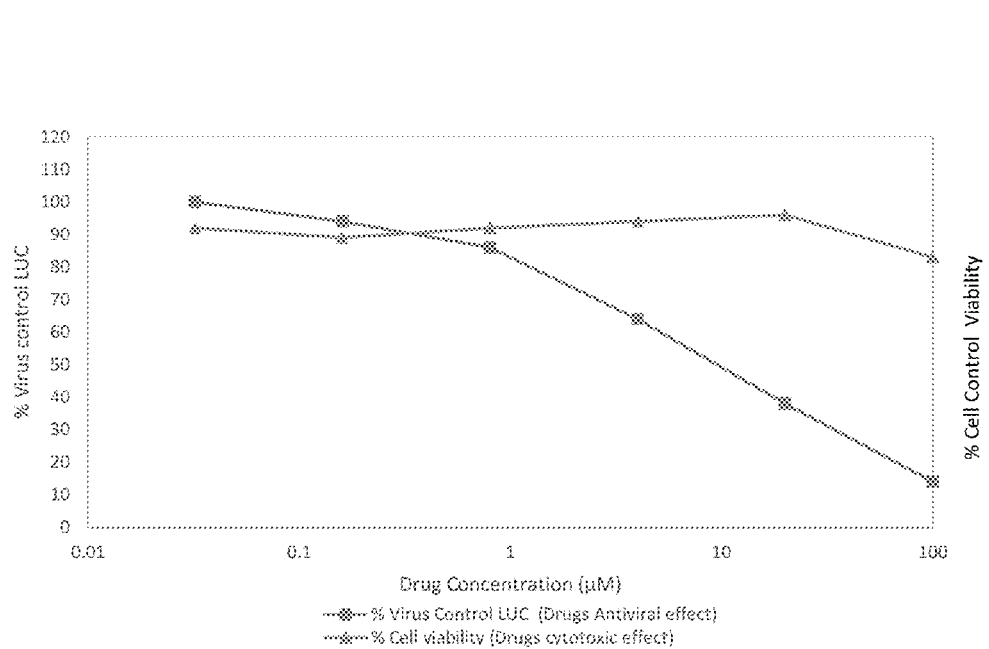
FIG. 2 includes a graph of Prasugrel in HCVcc assay

Hepatitis C is a complex disease of the liver. Due its widespread nature and global burden, this disease has always attracted attention for insight into its causative agent, hepatitis C virus (HCV), and for the development of new therapeutic approaches. Despite years of discovery, HCV continues to be a major cause of concern and a huge burden on public health systems worldwide.

The present invention contemplates the use of a pharmaceutical agent for the treatment of viral infection hepatitis C. In one embodiment, the pharmaceutical agent is a thienopyridine derivative. In one embodiment, the pharmaceutical agent is prasugrel.

Prasugrel was first disclosed in U.S. Pat. No. 5,288,726, and belongs to the class of thienopyridine adenosine diphosphate receptor antagonists. It is chemically designated as 5-[(1RS)-2-cyclopropyl-1-(2-fluorophenyl)-2-oxoethyl]-4,5,6,7-tetrahydrothieno[3,2-c]pyridin-2-yl acetate hydrochloride. It is sold in the United States as the hydrochloride salt under the name Effient®. The chemical structure of prasugrel hydrochloride is:

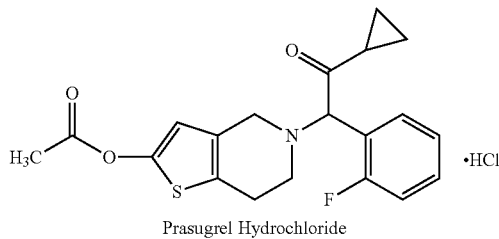 [SMILES: CC(=O)Oc1cc2c(s1)CCN(C(C(=O)C1CC1)c1ccccc1F)C2 ; Cl]

Prasugrel Hydrochloride

Prasugrel is an inhibitor of platelet activation and aggregation through the irreversible binding of its active metabolite to the P2Y12 class of ADP receptors on platelets. It reduces the aggregation ("clumping") of platelets by irreversibly binding to P2Y12 receptors.

Effient® indicated to reduce the rate of thrombotic cardiovascular (CV) events (including stent thrombosis) in patients with acute coronary syndrome (ACS) who are to be managed with percutaneous coronary intervention (PCI)-patients with unstable angina (UA) or non-ST-elevation myocardial infarction (NSTEMI), patients with ST-elevation myocardial infarction (STEMI) when managed with primary or delayed PCI.

Effient® is available in 5 mg and 10 mg tablets. Effient® 5-mg is available as a yellow, elongated hexagonal, film-coated, non-scored tablet and Effient® 10-mg is available as a beige, elongated hexagonal, film-coated, non-scored tablet. Initial dose of Effient® is with 60-mg oral loading doe and continue at 10-mg once daily with or without food. Consider 5-mg once daily for patients <60 kg. Patients are recommended to take aspirin (75-mg to 325-mg) daily. Prasugrel has been shown to reduce the rate of a combined endpoint of cardiovascular death, nonfatal myocardial infarction (MI), or nonfatal stroke compared to clopidogrel. It is generally recommended that antiplatelet therapy be administered promptly in the management of ACS because many cardiovascular events occur within hours of initial presentation.

Numerous methods of identifying the presence of Hepatitis C in patients or biological samples have been developed. These include, but are not limited to the compositions of matter, devices and methods as set forth in U.S. Pat. Nos. 5,580,718; 5,574,132; 5,597,691; 5,552,310; 5,514,539; and 5,595,868.

The inventors of the present invention have found that prasugrel has activity for the treatment of hepatitis C. Viral infections coincide with platelet activation, and a host's inflammatory response results in the release of platelet activating mediators and a pro-oxidative and a pro-coagulant environment which favors platelet activation. Thus, platelet activation not only occurs in response to injury, but also modulates host response and viral survival. Hence platelet activation inhibition is a promising approach for anti-viral therapy. Prasugrel, is an inhibitor of platelet activation and aggregation through the irreversible binding of its active metabolite to the P2Y12 class of ADP receptors on platelets, can modulate viral infection.

Treatment with prasugrel offers several advantages over other treatment schemes (e.g., interferon). Unlike interferon, prasugrel is potentially improving patient safety and compliance. Prasugrel is fairly well tolerated with few side effects, and is cost effective. Thus prasugrel may result in higher compliance with hepatitis C patients, improving overall outcomes.

The term "combination" as used herein, defines either a fixed combination in one dosage unit form, a non-fixed combination or a kit containing individual parts for combined administration.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a hepatitis C virus including viral resistance. Within the meaning of the present invention, the term "treat" also includes to arrest, delay the onset (i.e., the period prior to clinical manifestation of a disease) and/or reduce the risk of developing or worsening a disease.

The term "prasugrel" is used in broad sense to include not only "prasugrel" per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, and pharmaceutically acceptable polymorphs.

Pharmaceutically acceptable salts are salts that retain the desired biological activity of the parent compound and do not impart undesirable toxicological effects. Examples of such salts are acid addition salts formed with inorganic acids, for example, hydrochloric, hydrobromic, sulfuric, phosphoric, and nitric acids and the like; salts formed with organic acids such as acetic, oxalic, tartaric, succinic, maleic, fumaric, gluconic, citric, malic, methanesulfonic, p-toluenesulfonic, napthalenesulfonic, and polygalacturonic acids, and the like; salts formed from elemental anions such as chloride, bromide, and iodide; salts formed from metal hydroxides, for example, sodium hydroxide, potassium hydroxide, calcium hydroxide, lithium hydroxide, and magnesium hydroxide; salts formed from metal carbonates, for example, sodium carbonate, potassium carbonate, calcium carbonate, and magnesium carbonate; salts formed from metal bicarbonates, for example, sodium bicarbonate and potassium bicarbonate; salts formed from metal sulfates, for example, sodium sulfate and potassium sulfate; and salts formed from metal nitrates, for example, sodium nitrate and potassium nitrate. Pharmaceutically acceptable and non-pharmaceutically acceptable salts may be prepared using procedures well known in the art, for example, by reacting a sufficiently basic compound such as an amine with a suitable acid comprising a physiologically acceptable anion. Alkali metal (for example, sodium, potassium, or lithium) or alkaline earth metal (for example, calcium) salts of carboxylic acids can also be made. In certain embodiment prasugrel is provided as the hydrochloride salt.

Depending on the pathological stage, patient's age and other physiological parameters, and the extent of invasion, prasugrel may require specific dosage amounts and specific frequency of administrations. Preferably, prasugrel may be administered at least once, twice or thrice a day in an amount from 2 mg to 100 mg. In certain embodiments, the prasugrel is administered in a daily dose in an amount greater than 10 mg day. In some embodiments, prasugrel may be administered such that the total daily dose is in an amount from 5-100 mg, 10-100 mg, 15-100 mg, 20-100 mg, 25-100 mg, 30-100 mg, 35-100 mg, 40-100 mg, 45-100 mg, 50-100 mg, 10-50 mg, 15-50 mg, 20-50 mg, 25-50 mg, 30-50 mg, 35-50 mg, 40-50 mg, 10-25 mg, or 15-25 mg. In certain embodiments, prasugrel is administered in an amount that the total daily dose is greater than 10 mg. When prasugrel is administered as a pharmaceutically acceptable salt, the dose levels refer the equivalent amount of prasugrel free base. For instance, a dose level of 5 mg of prasugrel corresponds to 5.49 mg of prasugrel hydrochloride.

In some embodiments, prasugrel may be administered to a hepatitis C patient for a period of at least 2 weeks, at least 4 weeks, at least 6 weeks, at least 10 weeks, at least 12 weeks, at least 15 weeks, at least 20 weeks, at least 30 weeks, at least 40 weeks, or at least 52 weeks. In some instances, prasugrel may be administered for a period of 2-52 weeks, 2-104 weeks, or 2-208 weeks.

Preferably, prasugrel may be provided in the form of a pharmaceutical composition such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution and sprinkles, transdermal patches, however, other dosage forms such as controlled release formulations, lyophilized formulations, modified release formulations, delayed release formulations, extended release formulations, pulsatile release formulations, dual release formulations and the like. Liquid and semisolid dosage forms (liquids, suspensions, solutions, dispersions, ointments, creams, emulsions, microemulsions, sprays, patches, spot-on), parenteral, topical, inhalation, buccal, nasal etc. may also be envisaged under the ambit of the invention. Dosage forms may be administered orally, or by injection (IV, SC, IM).

Prasugrel may be used for the treatment of Hepatitis C in mammals in monotherapy mode or in a combination therapy (e.g., dual combination, triple combination etc.) mode such as, for example, in combination with one or more anti-hepatitis C drugs. In some instances, the prasugrel or combination therapy can be administered to patients that are not undergoing or recovering from percutaneous coronary intervention. In some embodiments, the hepatitis C patients do not have acute coronary syndrome, unstable angina or ST-elevation myocardial infarction.

The inventors of the present invention have also found that the solubility properties of prasugrel may be improved by nanosizing thus leading to better bioavailability and dose reduction of the drug.

In one embodiment, prasugrel may be present in the form of nanoparticles which have an average particle size of less than 2,000 nm, less than 1,800 nm, 1,600 nm, less than 1,400 nm, less than 1,200 nm, or less than 1,000 nm.

Suitable excipients may be used for formulating the dosage form according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, antimicrobial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

There is provided a method of alleviating or treating hepatitis C by administration of prasugrel optionally in combination with one or more anti-hepatitis C drugs.

Preferably, one or more anti-hepatitis C drugs that may be envisaged under the scope of the present invention may comprise from categories of anti-hepatitis C drugs for the treatment of hepatitis C such as, but not limited to, recombinant Human Interferon Alfa such as pegylated interferon alfa-2a or pegylated interferon alfa-2b (collectively "peginterferon" or "PEG"), nucleoside analogs for example ribavirin, direct acting antivirals (for example daclatasvir, boceprevir and telapravir), NS3/4A protease inhibitors (PIs) (for example simeprevir), nucleotide NS5B polymerase pnhibitors (for example sofosbuvir), NS5A Inhibitors (for example daclatasvir), non-nucleoside NS5B Polymerase Inhibitors (for example dasabuvir) or multi-class combination drugs (for example sofosbuvir/velpatasvir, ledipasvir/sofosbuvir, ombitasvir/paritaprevir/ritonavir, ombitasvir/paritaprevir/ritonavir and dasabuvir, elbasvir/grazoprevir, daclatasvir/asunaprevir/beclabuvir).

The use of prasugrel may preferably be associated with one or more of the above referenced anti-hepatitis C drugs as a combination therapy (either of the same functional class or other) depending on various factors like drug-drug compatibility, patient compliance and other such factors wherein the said combination therapy may be administered either simultaneously, sequentially, or separately for the treatment of hepatitis C.

Prasugrel may be provided with one or more anti-hepatitis drugs in the form of a kit, wherein the kit includes prasugrel and at least one other anti-hepatitis C drug, and instructions for their administration to a hepatitis C patient.

According to the present invention there is provided a pharmaceutical composition comprising prasugrel in combination with one or more anti-hepatitis C drugs.

In certain embodiments, the administration of prasugrel, either alone or in combination with one or more anti-hepatitis drugs, can lower detectable HCV-RNA levels in a hepatitis patient. For instance, methods disclosed herein can lower HCV-RNA levels by at least 10%, at least 20%, at least 30%, at least 4%, at least 50%, at least 60%, at least 70%, at least 80%, at least 90%, or at least 95% relative to HCV-RNA levels prior to initiating treatment. In some instances, prasugrel can be administered to a patient such no HCV-RNA is detectable in the patient after the treatment course is complete. HCV-RNA levels can be determined by quantitative, multi-cycle reverse transcriptase PCR. Such techniques are known, for instance in U.S. Pat. No. 6,172, 046, col. 4, line 50-col. 6, line 5, which is hereby incorporated by reference. As used herein, no detectable HCV-RNA describes a condition in which there are less than 100 copies per ml serum of the patient.

It may be well appreciated by a person skilled in the art that the pharmaceutical composition comprising prasugrel in combination with one or more anti-hepatitis C drugs may require specific dosage amounts and specific frequency of administrations specifically considering their individual established doses, the dosing frequency, patient adherence and the regimen adopted. As described herein, considering that there are various parameters to govern the dosage and administration of the combination composition as per the present invention, it would be well acknowledged by a person skilled in the art to exercise caution with respect to the dosage, specifically, for special populations associated with other disorders.

In order that this invention be more fully understood, the following preparative and testing methods are set forth. These methods are for the purpose of illustration only and are not to be construed as limiting the scope of the invention in any way.

EXAMPLES

Example 1

HCV Replicon Assay

Stable HCV replicons of different genotypes may be used for anti-HCV evaluation. We use the subgenomic HCV replicons of genotype 1a (H77 strain), 1b (Con1 strain), and 2a (JFH-1 strain), which are Huh7 human hepatoma cell lines that contains an HCV replicon.

The HCV replicon antiviral evaluation assay examines the effects of compound at six serial dilutions. Human interferon alpha-2b (rIFNα-2b) and Sofosbuvir are included in each run as a positive control compound.

Briefly, the replicon cells are plated at 5,000 cells/well into 96-well plates that are dedicated for the analysis of cell numbers (cytotoxicity) or antiviral activity. On the following day, samples are diluted with assay media and added to the appropriate wells. Cells are processed 72 hours later when the cells are still sub-confluent. For the luciferase endpoint assay, HCV replicon levels are assessed as replicon-derived Luc activity. The concentration of drug that reduces cell viability is assessed by the fluorometric CytoTox-1 cell proliferation assay (Promega), (expressed as cell numbers). For the qRT-PCR/TaqMan assay, total RNA is extracted from the replicon cells using RNeasy 96 kit (Qiagen) according to the manufacturer's protocol. Real-time RTPCR/TaqMan assays are performed to measure copy numbers of the replicon RNA and cellular ribosomal RNA. Where applicable $EC_{50}$ (concentration inhibiting HCV replicon by 50%), $EC_{90}$ (concentration inhibiting HCV replicon by 90%), $CC_{50}$ (concentration decreasing cell viability by 50%), $CC_{90}$ (concentration decreasing cell viability by 90%) and SI (selectivity indices: $CC_{50}/EC_{50}$ and $CC_{90}/EC_{90}$) values are derived.

Example 2

Infectious HCVcc Assay

Huh7.5 cells are grown in Dulbecco's modified essential media (DMEM), 10% fetal bovine serum (FBS), 1% penicillin-streptomycin (pen-strep), 1% Non-essential amino acids (NEAA) in a 5% $CO_2$ incubator at 37° C. Huh7.5 cells are seeded at $1\times10^4$ cells per well into 96-well plates according to Southern Research Institute standard format. Test articles are serially diluted with DMEM plus 5% FBS. The diluted compound in the amount of 50 μl is mixed with equal volume of cell culture-derived HCV (HCVcc), then applied to appropriate wells in the plate. Human interferon alpha-2b (rIFNα-2b) and/or Sofosbuvir are included as a positive control. After 72 hr incubation at 37° C., the cells are lysed for measurement of luciferase activity using Renilla Luciferase Assay System (Promega) according to manufacturer's instruction. The number of cells in each well is determined by CytoTox-1 reagent (Promega). Test articles are tested at 6 serial dilutions in triplicate to derive, if applicable, $EC_{50}$ and $EC_{90}$ (concentration inhibiting HCVcc infectivity by 50% and 90%, respectively), $CC_{50}$ (concentration decreasing cell viability by 50%) and SI (selectivity index: $CC_{50}/EC_{50}$) values (Table 0.1)

| Study | Study Title | $CC_{50}$ | $EC_{50}$ | Prasugrel (Selectivity index) |
|---|---|---|---|---|
| In vitro | In vitro HCV replicon assay | 88.5 | 47.1 | 1.88 |
| In vitro | In vitro HCV cc assay | >100 | 9.71 | >10.3 |

Example 3

Dosage Forms

| | Dosage Form A | | |
|---|---|---|---|
| | | Qty/Unit (mg) | |
| Sr. No. | Ingredients | 5.0 mg | 10.0 mg |
| | Strength | | |
| 1. | Prasugrel | 5.00 | 10.00 |
| 2. | Mannitol | 45.00 | 90.00 |
| 3. | Microcrystalline Cellulose | 61.00 | 122.00 |
| 4. | Hypromellose | 30.00 | 60.0 |
| 5. | Croscarmellose Sodium | 7.50 | 15.00 |
| 6. | Magnesium stearate | 1.50 | 3.00 |
| | Coating | | |
| 7. | Opadry II White | 6.00 | 12.00 |

Process:
1. Prasugrel and Mannitol, Microcrystalline cellulose, Hypromellose, Croscarmellose sodium was co-sifted through suitable mesh sieve.
2. Pre-sifted ingredients obtained in Step1 were loaded in Saizoner or Rapid mixer granulator and granulated using suitable solvent.
3. The granules obtained in step 2 were dried and sized through Co-mill using suitable Screen and sieve size.
4. The dried and sized granules obtained in step 3 were lubricated with pre-sifted magnesium stearate in a suitable blender.
5. The lubricated granules obtained in step 4 were compressed Coating solution was prepared by dissolving the Opadry II white in Purified water and the compressed tablets obtained in step 6 were coated till the desired weight gain.

| Dosage Form B | | | |
|---|---|---|---|
| | | Qty/Unit (mg) | |
| Sr. No. | Ingredients | 5.0 mg | 10.0 mg |
| | Strength | | |
| 1. | Prasugrel | 5.00 | 10.00 |
| 2. | Mannitol | 45.00 | 90.00 |
| 3. | Microcrystalline Cellulose | 60.00 | 120.00 |
| 4. | Hypromellose | 30.00 | 60.00 |
| 5. | Low-Substituted hydroxypropyl cellulose | 7.00 | 14.00 |
| 6. | Glyceryl dibehenate | 3.00 | 6.00 |
| | Coating | | |
| 7. | Opadry II White | 6.00 | 12.00 |

Process:
1. Prasugrel and Mannitol, Microcrystalline cellulose, Hypromellose, Croscarmellose sodium were co-sifted through suitable mesh sieve.
2. The pre-sifted ingredients obtained in step 1 were loaded in Saizoner or Rapid mixer granulator and granulated using suitable solvent.
3. The granules obtained in step 2 were dried and milled through Co-mill using suitable Screen and sieve size.
4. The dried and sized granules obtained in step 3 were lubricated with the pre-sifted magnesium stearate and in a suitable blender.
5. The lubricated granules obtained in step 4 were compressed.
6. Opadry II white was dissolved in Purified water and the compressed tablets obtained in step 5 were coated till the desired weight gain.

| Dosage Form C | | | |
|---|---|---|---|
| | | Qty/Unit (mg) | |
| Sr. No. | Ingredients | 5.0 mg | 10.0 mg |
| | Strength | | |
| 1. | Prasugrel | 5.0 | 10.0 |
| 2. | HPMC K100 M CR | 18.0 | 36.0 |
| 3. | Lactose monohydrate | 29.6 | 59.2 |
| 4. | HPMC K4 M | 24.0 | 48.0 |
| 5. | Croscarmellose sodium | 3.6 | 7.2 |
| 6. | Microcrystalline Cellulose | 18.0 | 36.0 |
| 7. | Magnesium Stearate | 1.8 | 3.6 |
| | Coating | | |
| 8. | Opadry II White | 6.00 | 12.00 |

Process:
1. Prasugrel, HPMC K100 M CR, HPMC K4 M and lactose monohydrate were cosifted through suitable mesh sieve.
2. Pre-sifted ingredients obtained in step 1 were loaded in a Saizoner or Rapid mixer granulator and granulated using suitable solvent.
3. The granules obtained in step 2 were dried and sized through Co-mill using suitable Screen and sieve size.
4. The granules obtained in step 4 were blended with the pre-sifted Croscarmellose sodium, Microcrystalline Cellulose and in a suitable blender.
5. The blended granules obtained in step 5 were lubricated using pre-sifted Magnesium Stearate in a suitable blender.
6. The lubricated granules obtained in step 6 were compressed.
7. Opadry II white was dissolved in Purified water and the compressed tablets obtained in step 7 were coated till the desired weight gain.

| Dosage Form D | | |
|---|---|---|
| Sr. No. | Ingredients | Quantity mg/capsule |
| 1. | Prasugrel | 2.5-50 |
| 2. | Pregelatinized corn starch | 10-150 |
| 3. | Colloidal silicon dioxide | 1-15 |
| 4. | Magnesium stearate | 3-10 |
| 5. | Talc | 3-10 |
| 6. | Empty hard gelatin capsule | 1 unit |

Process:
1. Prasugrel was sifted through suitable mesh sieve.
2. Pregelatinized corn starch, Colloidal silicon dioxide and talc were sifted through suitable mesh sieve.
3. The sieved powders of step 1 &2 were loaded in the blender and mixed for approximately 10 minutes.
4. Magnesium stearate was sifted and were blended with the powder obtained in step 3 for approximately 5 minutes
5. The blend obtained in step 4 were filled in the empty hard gelatin capsule shells using a capsule filling machine.
Note: The processing area must be under controlled room temperature and humidity. The limits are RH 50% to 55%, temperature 22° C. to 27° C.

| Dosage Form E | | |
|---|---|---|
| Sr. No. | Ingredients | Quantity mg/tablet |
| 1. | Prasugrel | 2.5-50 |
| 2. | Lactose monohydrate | 30-150 |
| 3. | Microcrystalline cellulose (Avicel PH 101) | 40-160 |
| 4. | Pregelatinized starch | 30-60 |
| 5. | Croscarmellose sodium | 15-45 |
| 6. | Poloxamer 188 (Pulmonic F 68) | 5-20 |
| 7. | Silicon dioxide colloidal | 2.5-10 |
| 8. | Magnesium stearate | 3-10 |
| 9. | Purified water | q.s |

Process:
1. Prasugrel, lactose, pregelatinized starch, and a portion (one-half) of croscarmellose sodium were sifted through a suitable mesh sieve.
2. Powder obtained in step 1 is mixed in a suitable mixer or granulator for approximately 20 minutes.
3. Poloxamer 188 was dissolved in a sufficient quantity of purified water for wet granulation of powder obtained in step 2.
4. Granules obtained in step 3 were kept in fluidized-bed dryer until the LOD is 2% or less.
5. Dried granules obtained in step 4 were passed through screen to obtain granules of the desired size (1-3 mm) and blended with silicon dioxide (sifted through suitable mesh Sieve), microcrystalline cellulose (pre sifted through suitable mesh sieve), and the remaining croscarmellose sodium in an octagonal blender for approximately 7 minutes.
6. Lubrication of the blend was carried out by adding magnesium stearate (previously sifted through suitable mesh Sieve) to the blend of step 5 and further blending for 3 minutes.

7. The lubricated blend obtained in step 6 was compressed into tablets using suitable tooling using a tablet compression machine.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

The invention claimed is:

1. A method of treating hepatitis C infection in humans comprising administering a pharmaceutical composition comprising prasugrel or a pharmaceutically acceptable salt thereof to a patient in need thereof.

2. The method of claim 1, wherein prasugrel is administered daily in a dose from 2 mg to 100 mg per day.

3. The method of claim 1, further comprising administering at least one other anti-hepatitis C drug to the patient.

4. The method of claim 1, wherein the composition comprises prasugrel in an amount from 2-100 mg.

5. The method of claim 1, wherein the composition comprises at least one other anti-hepatitis C drug.

6. The method of claim 4, wherein the composition comprises prasugrel in an amount from 10-100 mg.

7. A pharmaceutical composition comprising prasugrel and at least one other anti-hepatitis C drug.

* * * * *